United States Patent [19]

Kurz

[11] 4,382,780

[45] May 10, 1983

[54] RADIO WAVE VIBRATIONAL ORTHODONTIC APPLIANCE

[76] Inventor: Craven H. Kurz, No. 6 North Star, Apt. 106, Marina del Rey, Calif. 90291

[21] Appl. No.: 379,052

[22] Filed: May 17, 1982

[51] Int. Cl.$^3$ ............................................. A61C 7/00
[52] U.S. Cl. ..................................................... 433/5
[58] Field of Search ........................................... 433/5

[56] References Cited

U.S. PATENT DOCUMENTS

| | | | |
|---|---|---|---|
| 4,229,165 | 10/1980 | Kurz | 433/5 |
| 4,244,688 | 1/1981 | Kurz | 433/5 |
| 4,348,177 | 9/1982 | Kurz | 433/5 |
| 4,348,178 | 9/1982 | Kurz | 433/5 |

*Primary Examiner*—Robert Peshock
*Attorney, Agent, or Firm*—Keith D. Beecher

[57] ABSTRACT

An orthodontic appliance is provided which applies a vibrational force to the tooth to be moved, rather than a continuous force as is the case with the usual prior art devices. The invention is predicated on the concept that when vibrational forces are applied to the tooth, there is little or no hyalinization and consequently more cellular activity giving rise to more oesteoclasts for bone resorption and more oesteoblasts for bone apposition. Moreover, the vibrational effect of the tooth on the adjacent periodontal membrane and bone tends to loosen their fibrous structure, and helps the tooth to find a path of least resistance through the bone. In the assembly of the present invention, the vibrational effect is produced by a radio and speaker mounted on an orthodontic appliance, or directly on the tooth, in response to radio waves transmitted by an adjacent radio transmitter.

6 Claims, 4 Drawing Figures

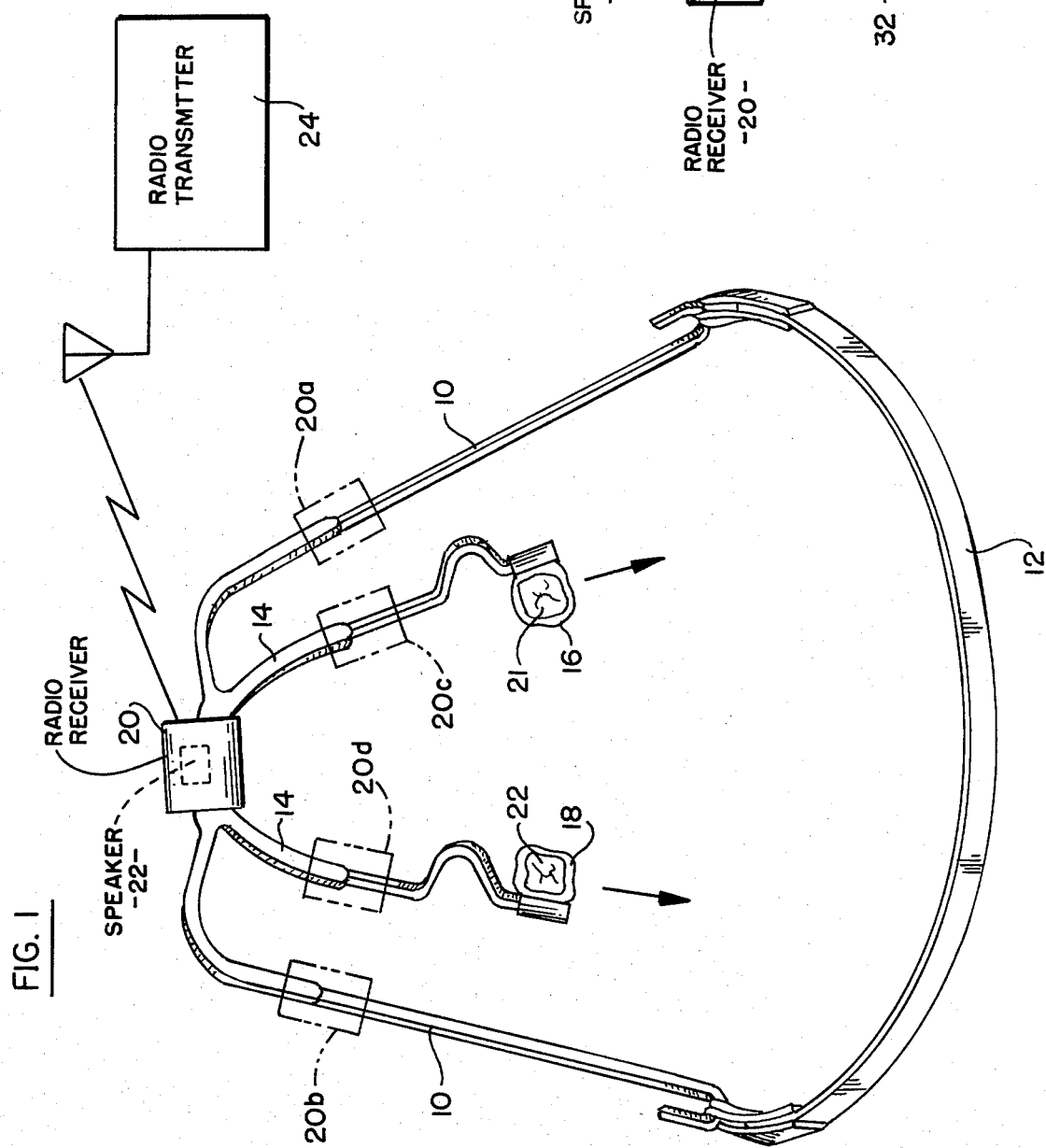

RADIO WAVE VIBRATIONAL ORTHODONTIC APPLIANCE

BACKGROUND OF THE INVENTION

The conventional method of orthodontic tooth movement, as practiced in the prior art, has been one of constant heavy or light pressure applied to the tooth in order to move the tooth through the adjacent bone. Constant pressure applied to the periodontal membrane by traditional orthodontic appliances causes the periodontal fibers to become cell-free which results in standstill of the tooth. Compression of tissue results in reduced blood supply and tissue necrosis, and the tooth will not move again until the bone subjacent to the hyalinized tissue has been eliminated by undermining resorption. Generally, it is essentially the magnitude of the force which will determine the duration of the hyalinization. Moreover, strong forces produce a wide hyalinization area of long duration. A discussion of this phenomenon may be found on pages 76 and 97 of Current Orthodontic Concepts and Techniques, T. M. Graber, Editor, published by W. B. Saunders & Co., 1969.

When a tooth is tipped by a continuous force exerted on it by the usual prior art orthodontic appliance, the periodontal membrane is compressed in a circumscribed area situated close to the alveolar crest. This area becomes cell-free and blood vessels are occluded. A description of this occurrence may be found, for example, at Page 497 of Orthodontic Principles and Practice by Graber, 2d Edition, published by Saunders & Co., 1967. If the pressurized area of the periodontal membrane during the movement of a tooth by an orthodontic device is not compressed by strong forces, then the formation of oesteoclasts, the cells responsible for resorption of bone, will be enhanced. The flow of blood to the area will not be restricted, and consequently oesteoclastic activity will become more vigorous and bone resorption will be increased.

Various orthodontic appliances are described and claimed in U.S. Pat. Nos. 4,123,844; 4,244,688 and 4,229,165, all of which have issued in the name of the present inventor, which introduce pressure impulses to the teeth being moved, rather than a continuous pressure. With every pressure impulse, the tissue pressure in the periodontal membrane and adjacent bone tissue will be increased. When the pressure is relaxed, the tissue fluid in the periodontal membrane and adjacent bone tissue will be reduced. This fluctuation from high pressure to low pressure in the periodontal and adjacent tissue will result in a pump-like action that will suck blood and tissue fluid into the area, and which will then expel fluid from the area, for each cycle of operation. This pulsation action serves to increase the cellular activity around the moving tooth, giving rise to more oesteoclasts for bone resorption and more oesteoblasts for bone apposition.

The active exchange of fluid during the pulsating operation of the appliances described in the patents helps to carry the by-products of bone resorption out of the resorption area. The pulsating tooth movement produced by such vibrational appliances in physiological and dynamic in nature, rather than pathological. Beacuse the pulsation pressure exerted by the appliances described in the patents does not result in areas of hyalinization and necrosis, there is no root resorption or horizontal bone loss during the operation. The pump-like action of the tooth being pulsed by the appliances described in the patents is the same on the tension side of the tooth as on the compression side, but opposite in the timing cycle. On the tension side of the tooth, the increased blood supply results in increased cellular activity.

The vibrational assembly of the present invention is constructed to produce the same pulsations as are produced by the systems described in the patents referred to above. However, vibrations are produced in the assembly of the present invention by a radio transmitter which radiates radio waves to a radio receiver mounted on an orthodontic appliance, or directly on the patient's tooth. The radio receiver responds to the radio waves from the transmitter to cause its speaker to vibrate and set up the desired vibrations for the tooth or teeth being treated. The receiver may be mounted, for example, on the external or internal bow of a headgear, or other orthodontic appliance, or, as noted above, the receiver may be mounted directly on the tooth being treated.

The frequency and amplitude of the speaker vibrations can be easily controlled by controlling the frequency and amplitude of the radio wave radiated by the transmitter. The transmitter itself may be kept in the same room as the patient, or carried by the patient when he is out of doors.

The effect of the radio wave radiated by the transmitter is to excite the speaker associated with the radio receiver, causing the speaker to vibrate. The vibrations of the speaker are introduced into the tooth or teeth being treated.

As mentioned above, the radio receiver may be mounted on an orthodontic appliance, or it may be made small enough to be mounted directly on the tooth being treated by means, for example, of a suitable adhesive, or on a metal band which is fixed to the tooth. Moreover, the radio receiver and speaker may be mounted on an orthodontic positioner, for example, of the type described in U.S. Pat. No. 4,123,844, to assist the normal action of the positioner.

BRIEF DESCRIPTION OF THE DRAWINGS

FIG. 1 shows one embodiment of the invention, which includes a radio receiver and speaker mounted on a posterior cervical extra-oral orthodontic appliance;

FIG. 2 is a representation of a tooth, having a miniature radio receiver and speaker mounted on an appropriate band which is wrapped around the tooth;

DETAILED DESCRIPTION OF THE ILLUSTRATED EMBODIMENTS

Figure 4:
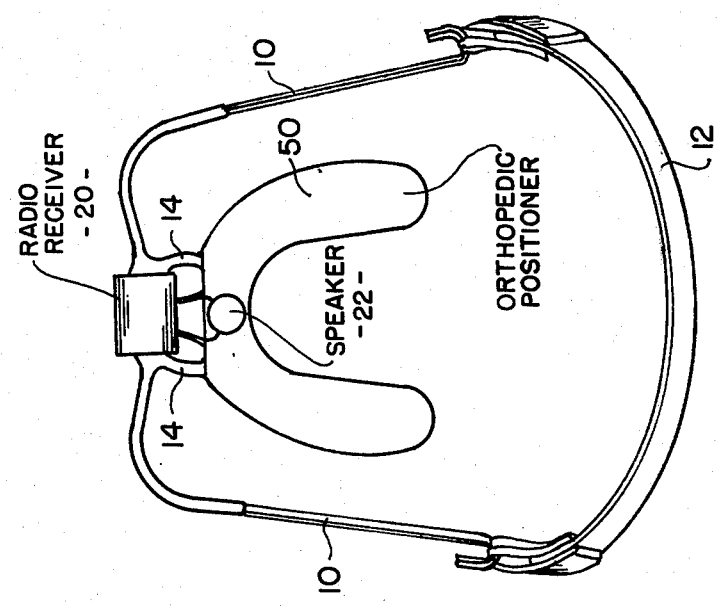
FIG. 4 shows the radio receiver and speaker mounted on an extra-oral orthodontic appliance used in conjunction with an orthopedic tooth positioner.

In the embodiment illustrated in FIG. 1, the assembly of the present invention is shown as used in conjunction with a cervical extral-oral orthodontic appliance. As shown in FIG. 1, a radio receiver 20 is mounted at the junction of an external extra-oral arch bow 10 and internal extra-oral arch bow 14 of an orthodontic appliance, which includes a usual elastic retaining band 12 which extends around the back of the head or neck of the patient. The ends of the inner bow 14 are coupled to the usual tooth bands 16 and 18 which are mounted on molars 21 and 23 which are to be moved distally by the appliance.

In accordance with the present invention, and as mentioned above, the radio receiver 20 is mounted, for example, at the junction of the external and internal bows 10, 14. The radio includes a speaker 22 which is caused to vibrate when the radio receiver receives a radio wave from a radio transmitter 24. The radio transmitter, as mentioned above, may be positioned in the room in which the patient is being treated, or it may be carried by the patient. The frequency and amplitude of the wave transmitted from transmitter 24 to radio receiver 20 may be controlled by any appropriate control means so that a desired frequency and amplitude may be achieved.

When the radio wave is received by the receiver 20, speaker 22 vibrates, which establishes a pulsating pressure on the molars 21 and 23 through the inner arch bow 14. As an alternative, two radio receivers 20a, 20b may be mounted respectively, as shown, on the external arch bow, each equipped with an associated speaker (not shown). As a further alternative, a pair of receivers 20c, 20d may be mounted on the internal arch bow 14, each equipped with an appropriate speaker (not shown). In either event, when the particular receiver is excited by radio waves of radio transmitter 24, the resulting vibrations set up in its speaker are transmitted through the orthodontic appliance to the molars 21 and 23, to move the molars distally, as indicated by the arrows.

In the embodiment of FIG. 2, the radio receiver 20, and its associated speaker 22 are adhesively, or otherwise attached to a metallic band 30, the band being wrapped around a tooth 32.

The tooth 32 may be attached to any appropriate orthodontic appliance to produce desired movement of the tooth. During the movement of the tooth, pulsations are set up by activating speaker 22, through radio receiver 20, so that the speaker will vibrate.

Figure 3:
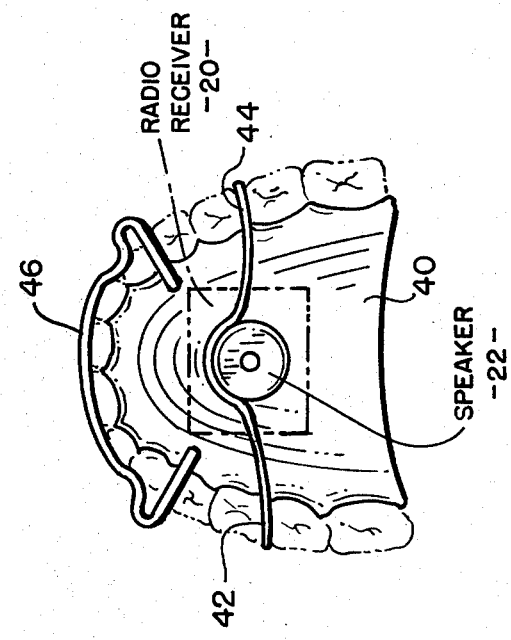
FIG. 3 shows a radio receiver and speaker mounted, in accordance with the further embodiment of the invention on an intra-oral orthodontic appliance.

In the embodiment of FIG. 3, the radio receiver 20 is mounted on a conventional intra-oral orthodontic appliance 40, with the speaker 22 positioned as shown. The intra-oral appliance includes an acrylic mouthpiece which fits into the mouth over the palate. A pair of spring arms 42 and 44 extend from the speaker 22 between the teeth, as shown. A labial bow 46 is also mounted in the illustrated position.

Pressures are applied medially and distally using the mouthpiece of the appliance 40 as anchorage. When posterior teeth are to be moved in the mesial direction, the labial bow 68 embraces the anterior teeth using them as anchorage for this type of movement. The spring arms 64 and 66 may be adjusted so that they are capable of contacting and moving any of the teeth mesially, distally, bucally or lingually.

The appliance of FIG. 3 is removable, and it is worn only at the patient's convenience. When the appliance is in place, the radio transmitter 24 of FIG. 1 may be used to transmit radio waves to receiver 20, so as to establish vibrations in speaker 22 which, in turn, causes the teeth being treated to pulsate, for the reasons described above.

In the embodiment of FIG. 4, the radio receiver 20 is mounted at the junction of the inner and outer bows 10, 14 of the headgear appliance, and the speaker 22 is mounted in a rubber orthopedic positioner 50. The positioner 50 is of the usual type which is carried in the mouth of the patient, and which has tooth socket impressions, so that there is a tendency when the positioned is being worn, for the teeth of the wearer to be forced into the proper orientations and inclinations, as established by the sockets in the positioner 50. As in the previous embodiments, the speaker 22 may be vibrated by radio waves from transmitter 24 of FIG. 1 to set up desired pulsations in the positioner to assist in the orthodontic action.

It will be evident from the foregoing description that the receiver and speaker used in the assembly of the present invention may be mounted on a variety of different types of orthodontic appliances, and may also be mounted directly on the tooth being treated, as shown in FIG. 2.

Accordingly, although particular embodiments of the invention have been shown and described, modifications may be made, and it is intended in the claims to cover all modifications which come within the true spirit and scope of the invention.

What is claimed is:

1. An orthodontic appliance comprising: an element for engaging a tooth to be moved and serving to apply a force to the tooth to move the tooth in a predetermined direction in the mouth of the patient; a radio receiver mounted on the appliance for receiving a radio wave of a predetermined amplitude and frequency, and a speaker included in the radio receiver which vibrates upon the receipt of the radio receiver of the radio wave to cause said element to exert a pulsating force on the tooth.

2. The orthodontic appliance defined in claim 1, in which said element is an internal bow of an orthodontic headgear appliance which also has an external bow, and said radio receiver and speaker are mounted on the junction of the internal and external bows to establish pulsations in the internal bow.

3. The orthodontic appliance defined in claim 1, in which said element is a band extending around the tooth, and in which said radio receiver and speaker are mounted on said band.

4. The orthodontic appliance defined in claim 1, in which said appliance includes a solid mouthpiece, and said radio receiver and speaker are mounted on said mouthpiece.

5. The orthodontic appliance defined in claim 1, and which includes an orthopedic positioner, and in which said speaker is mechanically coupled to said positioner.

6. The orthodontic appliance defined in claim 2, and which includes an orthopedic positioner mounted on said internal bow.

* * * * *